(12) United States Patent
Halloran et al.

(10) Patent No.: US 6,201,091 B1
(45) Date of Patent: Mar. 13, 2001

(54) ORGANOFUNCTIONAL COCYCLIC SILOXANES AND POLYMERIZATION THEREOF

(75) Inventors: Daniel Joseph Halloran; Brett Lee Zimmerman, both of Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/378,058

(22) Filed: Aug. 20, 1999

(51) Int. Cl.[7] ............................ C08G 77/06; C08G 77/04
(52) U.S. Cl. ........................... 528/13; 528/12; 528/15; 528/16; 528/25; 528/37
(58) Field of Search .................. 528/12, 13, 15, 528/16, 25, 37

(56) References Cited

U.S. PATENT DOCUMENTS

| | | | |
|---|---|---|---|
| 4,587,320 | 5/1986 | Swihart | 528/23 |
| 6,071,975 | * 6/2000 | Halloran | 516/58 |
| 6,118,014 | * 9/2000 | Halloran et al. | 556/439 |

* cited by examiner

Primary Examiner—Richard D. Lovering
Assistant Examiner—Daniel S. Metzmaier
(74) Attorney, Agent, or Firm—James L. De Cesare

(57) ABSTRACT

An organofunctional cocyclic siloxane, i.e., a dialkyl, alkyl carboxyalkyl cocyclic siloxane, is used to prepare copolymeric siloxane fluids, copolymeric siloxane gums, and terpolymeric siloxanes via three polymerization techniques. In one embodiment, the dialkyl, alkyl carboxyalkyl cocyclic siloxane is polymerized using a bulk polymerization technique. In another embodiment, the dialkyl, alkyl carboxyalkyl cocyclic siloxane is polymerized using an emulsion polymerization technique. In an additional embodiment, the dialkyl, alkyl carboxyalkyl cocyclic siloxane is polymerized using a microemulsion polymerization technique. The dialkyl, alkyl carboxyalkyl cocyclic siloxane most preferred is a dimethyl, methyl carboxyalkyl cocyclic siloxane.

4 Claims, No Drawings

ORGANOFUNCTIONAL COCYCLIC SILOXANES AND POLYMERIZATION THEREOF

The dialkyl, alkyl carboxyalkyl cocyclic siloxane, most preferably a dimethyl, methyl carboxyalkyl cocyclic siloxane, is used to prepare copolymeric siloxane fluids, copolymeric siloxane gums, and terpolymeric siloxanes, according to the three polymerization techniques.

BACKGROUND OF THE INVENTION

In bulk polymerization techniques for the preparation of carboxyalkylpolysiloxanes, it is not uncommon to react a vinyl functional siloxane with thioglycolic acid $HSCH_2COOH$, which reaction provides a sulfur containing carboxy functional polymer. However, the sulfur odor inherent in such materials precludes their widespread use. In contrast, and according to the present invention, a sulfur-free route to carboxyalkylpolysiloxanes is provided.

In emulsion and microemulsion polymerization techniques for the preparation of carboxyalkylpolysiloxanes, it is also not uncommon to employ a carboxyalkyl trialkoxysilane as one of the precursors in order to impart functionality to the siloxane polymer. However, carboxyalkyl trialkoxysilanes typically have a considerable solubility in water, and therefore only partially incorporate into the siloxane polymer droplets formed during the ring opening polymerization reaction. As a consequence, one can only expect a low level of the carboxyalkyl trialkoxysilane to become incorporated into the siloxane polymer. In addition, the carboxyalkyl trialkoxysilane generates a significant amount of alcohol as a by-product, most commonly methanol, according to the reaction:

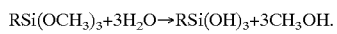

$$RSi(OCH_3)_3 + 3H_2O \rightarrow RSi(OH)_3 + 3CH_3OH.$$

While methanol is not classified as carcinogenic, it can be acutely toxic if ingested, and may even be fatal or result in blindness. Methanol is a general irritant to the skin and mucous membranes, and prolonged skin contact with methanol vapor or liquid can cause dermatitis. Therefore, it would be advantageous in applications especially in the personal care arena, to eliminate its presence.

In contrast, and according to the present invention, one can expect that the extent of incorporation of carboxy functionality into the siloxane polymer will improve with the use of the dialkyl, alkyl carboxyalkyl cocyclic siloxane due to its increased nonpolarity and hence its decreased water solubility. In addition, the dialkyl, alkyl carboxyalkyl cocyclic siloxane liberates no by-product of any kind.

Lastly, carboxyfunctional siloxanes are useful in the treatment of substrates such as hair and textiles, due to their siloxane lubrication properties, and durability imparted by the carboxy group. However, odor issues, i.e., sulfur containing, and poor process economics have generally hindered their widespread use in these commercial applications. This invention improves both the odor profile and the process economics.

BRIEF SUMMARY OF THE INVENTION

In a first embodiment, silicone copolymers and silicone terpolymers are prepared by bulk polymerization according to a method comprising heating a mixture of (i) an organofunctional cocyclic siloxane; and optionally (ii) a $C_8$ or more carbon atom containing alkylmethyl, dimethyl silicone cocyclic, in the presence of (iii) an acid catalyst, at a temperature and for a time sufficient to cause polymerization of (i) and optionally (ii) to the desired silicone copolymer and silicone terpolymer, respectively. The reaction mixture can further include (iv) a short chain linear silicone endblocker, (v) a dialkyl cyclosiloxane, or mixtures thereof.

In a second embodiment, there is provided a process of emulsion polymerization in which the polymerization reaction involves opening of polysiloxane rings of a cyclic organosilicon precursor using an anionic catalyst or a cationic catalyst in the presence of water, to form higher molecular weight polysiloxanes in the emulsion. The improvement according to the second embodiment comprises the use of an organofunctional cocyclic siloxane as the cyclic organosilicon precursor in the reaction mixture.

As in the first embodiment, the reaction mixture can further include the $C_8$ or more carbon atom containing alkylmethyl, dimethyl silicone cocyclic, the short chain linear silicone endblocker, the dialkyl cyclosiloxane, or mixtures thereof.

The third embodiment is a classical method of microemulsion formation involving mixing an oil and water with a surfactant (S1), and a co-surfactant (S2). The oil is an organofunctional cocyclic siloxane. The oil is added to a solution of the surfactant (S1) and water. A two-phase system containing the siloxane results. The two-phase system is then titrated with co-surfactant (S2) until a clear isotropic microemulsion results. An emulsion polymerization catalyst is added to the clear isotropic microemulsion, and polymerization of the cocyclic siloxane is initiated. The polymerization is allowed to advance until the reaction is complete, or a desired degree of polymerization (DP) has been obtained. Microemulsions of high molecular weight silicone polymers with low polydispersity can be produced.

As in the first and second embodiments, the reaction mixture can further include the $C_8$ or more carbon atom containing alkylmethyl, dimethyl silicone cocyclic, the short chain linear silicone endblocker, the dialkyl cyclosiloxane, or mixtures thereof.

These and other features of the invention will become apparent from a consideration of the detailed description.

DETAILED DESCRIPTION OF THE INVENTION

Copolymeric siloxane fluids, copolymeric siloxane gums, and terpolymeric siloxanes, are prepared by polymerizing an organofunctional cocyclic siloxane using a bulk polymerization technique, an emulsion polymerization technique, or a microemulsion polymerization technique.

The Organofunctional Cocyclic Siloxane

The organofunctional cocyclic siloxane used as a precursor in accordance with the present invention is a composition of matter having the formula

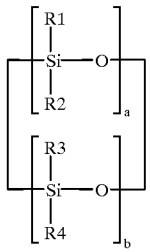

where R1 to R3 are each an alkyl group containing 1–6 carbon atoms; R4 is a carboxyalkyl or carboxyalkyl derivative group having the formula $—(CHR5)_nCOOR6$ where R5 is hydrogen or an alkyl group containing 1–6 carbon atoms; R6 is hydrogen, an alkyl group containing 1–6 carbon atoms, or a trialkylsilyl group —Si(R7)$_3$ in which R7 is an alkyl group containing 1–6 carbon atoms; a and b are each a positive integer having a value of 1–10; and n is a positive integer having a value of 3–20.

This organofunctional cocyclic siloxane, and methods for its preparation, are described in detail in copending U.S. patent application Ser. No. 09/354,675, filed Jul. 16, 1999, now U.S. Pat. No. 6,118,014, in the name of Daniel J. Halloran and Brett L. Zimmerman, entitled "*Organofunctional Cocyclic Siloxanes*". The copending application is assigned to the same assignee as the present application, and is considered incorporated herein by reference. Such compositions, as explained in detail in the copending application, are prepared by a hydrosilation process in which an ≡SiH containing cocyclic siloxane is contacted with an alkenoic acid such as undecylenic acid H$_2$C=CH(CH$_2$)$_8$COOH, in the presence of a Group VIII transition metal catalyst such as platinum.

The organofunctional cocyclic siloxane precursors used in the accompanying examples of this application had a structure generally corresponding to the formula

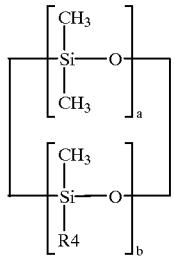

wherein R4 was the group —(CH$_2$)$_{10}$COOH, a had a value of 4, and b had a value of one.

Bulk Polymerization of an Organofunctional Cocyclic Siloxane

In this embodiment, polymerization of the organofunctional cocyclic siloxane yielded (i) trialkylsiloxy terminated silicone copolymers containing dialkyl and carboxyalkyl repeating units, and (ii) trialkylsiloxy terminated silicone terpolymers containing dialkyl, higher (C8+) alkylmethyl, and carboxyalkyl repeating units. These compositions corresponded generally to polymers of the formula:

wherein R is an alkyl group containing one to four carbon atoms, preferably methyl; R' is an alkyl group containing at least 8 carbon atoms; x and z each have a value of 1–1000; y has a value of 0–1000; R" is a carboxyalkyl or carboxyalkyl derivative group having the formula —(CHR5)$_n$COOR6 where R5 is hydrogen or an alkyl group containing 1–6 carbon atoms; R6 is hydrogen, an alkyl group containing 1–6 carbon atoms, or a trialkylsilyl group 13 Si(R7)$_3$ in which R7 is an alkyl group containing 1–6 carbon atoms; and n is a positive integer having a value of 3–20.

Bulk polymerization processes are generaly described in detail in copending U.S. patent application Ser. No. 09/262,938, filed Mar. 5, 1999, now U.S. Pat. No. 6,136,938, in the name of Daniel J. Halloran, entitled "*Silicone Terpolymers Containing Dimethyl, Higher Alkyl, and Aminoalkyl Repeating Units*". The copending application is assigned to the same assignee as the present application, and is considered incorporated herein by reference. Such processes, as explained in detail in the copending application, involve polymerizing and copolymerizing cyclic type siloxane species at elevated temperatures, in the presence of a catalyst, for a time sufficient to obtain the desired state of polymerization to polymers of essentially linear construction, i.e., the ring opening polymerization mechanism.

In particular, the method of producing polymers according to this embodiment of the present invention involves heating a mixture of (i) the organofunctional cocyclic siloxane, and when terpolymers are desired, (ii) a C$_8$ or more carbon atom containing alkylmethyl, dimethyl silicone cocyclic, in the presence of (iii) an acid catalyst, at a temperature and for a time sufficient to cause copolymerization of (i) and (ii) to the desired silicone polymer. The reaction mixture can include as optional ingredients (iv) a short chain linear silicone endblocker, (v) a dialkyl cyclosiloxane, or mixtures thereof.

The C$_8$ or more carbon atom containing alkylmethyl, dimethyl silicone cocyclic (ii) to be copolymerized is a composition having a structure generally corresponding to the formula:

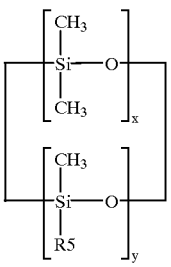

where x and y represent integers each having a value of 1–10, and R5 represents a group containing eight or more carbon atoms such as —(CH$_2$)$_7$CH$_3$, —(CH$_2$)$_{11}$CH$_3$, or —(CH$_2$)$_{15}$CH$_3$. R5 it is noted may be a hydrocarbon group containing more than sixteen carbon atoms, if desired.

The acid catalyst (iii) can be a mineral acid such as sulfuric acid or hydrochloric acid; an acid clay such as sulfuric acid activated montmorillonite clay; a Lewis acid such as ferric chloride FeCl$_3$, aluminum chloride AlCl$_3$, or boron trifluoride BF$_3$; an alkane sulfonic acid, i.e., RSO$_3$H, such as mixtures of methane, ethane, and propane sulfonic acids; or a perfluoroalkane sulfonic acid, i.e., C$_n$F$_{2n+1}$SO$_3$H where n is generally 1–30, but preferably less than about 20, such as trifluoromethane sulfonic acid (triflic acid CF$_3$SO$_3$H). Triflic acid is the preferred catalyst according to the present invention.

The optional short chain linear silicone endblocker (iv) is a composition of the type MD$_e$M, wherein "e" generally has a value of from 0 to about 8; "M" represents monofunctional unit (CH$_3$)$_3$SiO$_{1/2}$; and "D" represents difunctional unit (CH$_3$)$_2$SiO$_{2/2}$. This fourth optional component can be any one or more of linear alkyl siloxanes such as hexamethyldisiloxane (MM) with a boiling point of 100° C., viscosity of 0.65 mm$^2$/s, and formula Me$_3$SiOSiMe$_3$; octamethyltrisiloxane (MDM) with a boiling point of 152° C., viscosity of 1.04 mm$^2$/s, and formula Me$_3$SiOMe$_2$SiOSiMe$_3$; decamethyltetrasiloxane (MD$_2$M) with a boiling point of 194° C., viscosity of 1.53 mm$^2$/s, and formula Me$_3$SiO(Me$_2$SiO)$_2$SiMe$_3$; dodecamethylpentasiloxane (MD$_3$M) with a boiling point of 229° C., viscosity of 2.06 mm$^2$/s, and formula Me$_3$SiO(Me$_2$SiO)$_3$SiMe$_3$; tetradecamethylhexasiloxane (MD$_4$M) with a boiling point of 245° C., viscosity of 2.63 mm$^2$/s, and formula Me$_3$SiO(Me$_2$SiO)$_4$SiMe$_3$; and hexadecamethylheptasiloxane (MD$_5$M) with a boiling point of 270° C., viscosity of 3.24 mm$^2$/s, and formula Me$_3$SiO(Me$_2$SiO)$_5$SiMe$_3$.

When the short chain linear silicone endblocker (iv) is included in the reaction mixture, its presence results in the formation of trialkylsiloxy endblocked silicone copolymers and silicone terpolymers, rather than silanol endblocked silicone copolymers and silicone terpolymers as would be the case in its absence.

The optional dialkyl cyclosiloxane (v) can be any one or a mixture of cyclic siloxanes having the formula:

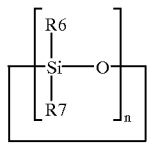

where n has a value of 3–6, and R6 and R7 each represent alkyl groups containing 1–6 carbon atoms. Preferably, R6 and R7 are each a methyl group.

Representative of such compositions (v) include, for example, hexamethylcyclotrisiloxane (D$_3$) a solid with a boiling point of 134° C. and formula $\{(Me_2)SiO\}_3$; octamethylcyclotetrasiloxane (D$_4$) with a boiling point of 176° C., viscosity of 2.3 mm$^2$/s, and formula $\{(Me_2)SiO\}_4$; decamethylcyclopentasiloxane (D$_5$) with a boiling point of 210° C., viscosity of 3.87 mm$^2$/s, and formula $\{(Me_2)SiO\}_5$; and dodecamethylcyclohexasiloxane (D$_6$) with a boiling point of 245° C., viscosity of 6.62 mm$^2$/s, and formula $\{(Me_2)SiO\}_6$. Its presence in the reaction medium merely provides an avenue enabling the use of lesser amounts of the essential components (i) and (ii).

EXAMPLES

Bulk Polymerization

The following examples are set forth in order to illustrate the first embodiment of this invention in more detail.

Example 1

Preparation of a Silicone Copolymer Fluid

In this example, a silicone copolymer was prepared having a structure generally corresponding to the formula:

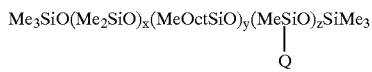

wherein Me represents the methyl group, Oct represents the octyl group CH$_3$(CH$_2$)$_7$—, and Q represents the group —(CH$_2$)$_{10}$COOH. In this example, however, the value of y was zero. The degree of polymerization (DP) was 100, i.e., the value of x+z=100.

Into a reaction vessel, a mixture was formed by adding to the reaction vessel 30.0 gram of the dimethyl, methyl carboxyalkyl cocyclic siloxane, 2.8 gram of a 5 centistoke (mm$^2$/s) polydimethylsiloxane as the short chain linear silicone endblocker, and 0.025 gram of trifluoromethane sulfonic acid catalyst. The initial viscosity of this mixture before polymerization was measured and determined to be about 29.5 centipoise (mm$^2$/s). The reaction vessel containing these ingredients was purged with nitrogen, and then heated to about 100° C. for about 5 hours. The reaction vessel was allowed to cool to less than about 50° C., and then the contents of the reaction vessel were neutralized with sodium hydroxide. Following neutralization, the contents of the reaction vessel were filtered. The final viscosity of the mixture after polymerization was measured and determined to be about 1,240 centipoise (mm$^2$/s).

Example 2

Preparation of a Silicone Copolymer Gum

Example 1 was repeated except that the amounts and the conditions used during the polymerization reaction were varied. Thus, the mixture was formed by adding to the reaction vessel 15.0 gram of the dimethyl, methyl carboxyalkyl cocyclic siloxane, and 0.013 gram of the trifluoromethane sulfonic acid catalyst. The initial viscosity of the mixture was the same as Example 1, i.e., 29.5 centipoise (mm$^2$/s). However, the reaction vessel was only heated for about 0.5 hour. The final viscosity of the mixture was about 1,698,624 centipoise (mm$^2$/s). The silicone copolymer which was prepared in this example had a degree of polymerization (DP) of about 3,400, which was an estimate based on its viscosity.

Example 3

Preparation of a Silicone Terpolymer Fluid

A silicone terpolymer was prepared having the formula:

wherein Me represents the methyl group, Oct represents the octyl group CH$_3$(CH$_2$)$_7$—, and Q represents the group —(CH$_2$)$_{10}$COOH. The DP was 50, i.e., the value of x+y+z=50.

In this example, a mixture was formed by adding to a reaction vessel 9.8 gram of the dimethyl, methyl carboxyalkyl cocyclic siloxane, 7.2 gram of a 5 centistoke (mm$^2$/s) polydimethylsiloxane as the short chain linear silicone endblocker, 38.1 gram of the C$_8$ carbon atom containing alkylmethyl, dimethyl silicone cocyclic, and 0.013 gram of trifluoromethane sulfonic acid catalyst. The initial viscosity of the mixture was about 6.9 centipoise (mm$^2$/s). The reaction vessel was purged with nitrogen, and heated to about 80° C. for 4 hours. The reaction vessel was cooled to less than about 50° C., and then the contents were neutralized with sodium hydroxide. Following neutralization, the contents were filtered. The final viscosity was about 22.6 centipoise (mm$^2$/s). The non-volatile content of the mixture, i.e., the amount of the silicone terpolymer, was 90.2 percent.

Emulsion Polymerization of an Organofunctional Cocyclic Siloxane

In this embodiment, the polymerization of an organofunctional cocyclic siloxane yielded an emulsion containing a silanol endblocked silicone copolymer having dialkyl and carboxyalkyl repeating units. An emulsion containing a silicone terpolymer having dialkyl, higher (C8+) alkylmethyl, and carboxyalkyl repeating units, can also be prepared according to this embodiment of the invention. The silicone copolymers and the silicone terpolymers in emulsions prepared according to this embodiment of the invention have a structure generally corresponding to formula:

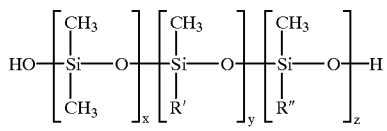

where x has a value of 1–2000; y has a value of 0–100; z has a value of 1–100; and R' and R" have the same meaning as defined above. As explained hereinafter, such polymers may be trialkylsiloxy endblocked instead of being silanol endblocked, if desired.

Emulsion polymerization processes, generally, are described in detail in copending U.S. patent application Ser. No. 09/349,359, filed Jul. 8, 1999 in the name of Daniel J. Halloran and Judith M. Vincent, entitled "Emulsion Polymerization Using a Cocyclic Silicone". The copending application is assigned to the same assignee as the present application, and is considered incorporated herein by reference.

Such processes, as explained in detail in the copending application, involve the opening of cyclic polysiloxane rings using an anionic or a cationic catalyst in the presence of water. The anions and the cations act as a polymerization catalyst for such reactions by functioning to open the ring of the cyclic polysiloxane, and allowing it to form linear siloxane oligomers having terminal hydroxy groups. These oligomers then react with other oligomers by means of a condensation reaction, with the result that higher molecular weight polysiloxanes are formed. A surfactant(s) is generally used to stabilize the polysiloxane in the emulsion in the form of small sized droplets.

In particular, the method according to this embodiment of the invention results in oil-in-water emulsions containing the copolymers and terpolymers which are made by (i) combining and mixing together certain organosilicon precursors, one or more surfactants, and water; (ii) optionally subjecting the mixture prepared in Step (i) to high shear; (iii) adding a catalyst to the mixture; (iv) heating the reaction mixture to initiate polymerization of the precursors; (v) cooling and neutralizing the mixture; and (vi) recovering an oil-in-water emulsion containing the silicone copolymer or the silicone terpolymer.

The organosilicon precursors which are used in the process according to this embodiment of the invention include as the essential ingredient, (i) the organofunctional cocyclic siloxane, i.e., the dialkyl, alkyl carboxyalkyl cocyclic siloxane. Optionally, the reaction mixture may also contain organosilicon precursors discussed above such as (ii) the $C_8$ or more carbon atom containing alkylmethyl, dimethyl silicone cocyclic, (iii) the short chain linear silicone endblocker, and (iv) the dialkyl cyclosiloxane.

Silicone copolymers according to this embodiment can be prepared using only the organosilicon precursor (i), while the silicone terpolymers require the presence of at least organosilicon precursors (i) and (ii). Silicone copolymers can also be prepared using organosilicon precursors (i) and (iv), if desired. When the short chain linear silicone endblocker (iii) is included in the reaction mixture, its presence results in the formation of trialkylsiloxy endblocked silicone copolymers and silicone terpolymers, rather than silanol endblocked silicone copolymers and silicone terpolymers, as would be the case in its absence.

A catalyst and a surfactant(s) are required for the reaction to proceed and for forming an emulsion, and reference may be had to the copending application for a detailed list of each of these components. However, it should be noted that certain acid catalysts such as dodecylbenzene sulfonic acid (DBSA) are capable of functioning as the acid catalyst as well as an anionic surfactant. When DBSA is used, therefore, it eliminates the need for using a separate acid catalyst and a separate anionic surfactant. Thus, DBSA will function as acid catalyst in the ring opening reaction, and then when the reaction is stopped and DBSA is neutralized, it will take on the characteristics of an anionic surfactant, i.e., sodium dodecylbenzene sulfonate, for purposes of forming the desired emulsion. In the accompanying example illustrative of this embodiment, DBSA was used as the catalyst, as well as the anionic the surfactant.

The method is carried out by creating a mixture of the ingredients including the organosilicon precursor(s), ionic (cationic or anionic) surfactant(s), optionally a nonionic surfactant(s), water, and catalyst. The mixture is heated with agitation at a polymerization reaction temperature until essentially all of the organosilicon precursor(s) have reacted, and a stable, oil-free emulsion of polymer is formed.

EXAMPLES

Emulsion Polymerization

The following examples are set forth in order to illustrate the second embodiment of this invention in more detail.

Example 4

Preparation of an Anionic Emulsion

The following ingredients in the amounts indicated were used to prepare a cationic emulsion using the emulsion polymerization technique according to this embodiment of the invention:

| Ingredients | Weight - Gram |
| --- | --- |
| Water | 513.00 |
| DBSA (anionic surfactant & catalyst) | 15.25 |
| Octamethylcyclotetrasiloxane, i.e., $D_4$ | 384.00 |
| Organofunctional Cocyclic Siloxane | 4.90 |

The ingredients were added to a flask and mixed at 300 rpm (31 rad/s) for 10 minutes. The mixture was homogenized in two passes at 5,000 psi (34,450 kPa), and 500 gram of homogenized mixture was added back to the flask, after processing it with an additional amount of 8.3 gram of DBSA. The contents of the flask was heated to 80° C. and the flask was maintained at 80° C. for four hours. The temperature of the flask was lowered to 45° C. for two hours. The contents of the flask was then neutralized.

A silicone was extracted from the emulsion and determined to have a structure generally corresponding to the formula

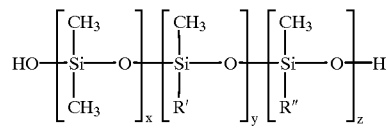

The silicone in Example 4 had the following characteristics.

| Characteristic | Value |
| --- | --- |
| Viscosity (mm²/s) | 55,800 |
| x | 1,000 |
| y | 0 |
| z | 2 |
| R' | Not applicable, i.e., y = 0. |
| R" | -(CH$_2$)$_{10}$COOH |

Microemulsion Polymerization of a Functional Cocyclic Siloxane

In this embodiment, the polymerization of an organofunctional cocyclic siloxane yielded a microemulsion containing a silanol endblocked silicone copolymer having dialkyl and carboxyalkyl repeating units. A microemulsion containing a silicone terpolymer having dialkyl, higher (C8+) alkylmethyl, and carboxyalkyl repeating units, can also be prepared according to this embodiment of the invention. The silicone copolymers and the silicone terpolymers in microemulsions prepared according to this embodiment of the invention have a structure generally corresponding to formula:

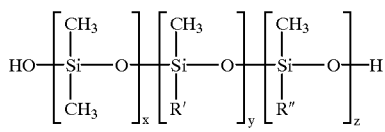

where x has a value of 1–2000; y has a value of 0–100; z has a value of 1–100; R' and R" have the same meaning as defined above. As explained above, such polymers may be trialkylsiloxy endblocked instead of being silanol endblocked, if desired.

Microemulsion polymerization processes, in general, are described in detail in copending U.S. patent application Ser. No. 09/227,838, filed Jan. 11, 1999, now U.S. Pat. No. 6,071,975, in the name of Daniel J. Halloran entitled "Method of Preparing Silicone Oil-In-Water Microemulsion". The copending application is assigned to the same assignee as the present application, and is considered incorporated herein by reference.

Such processes, as explained in detail in the copending application, provide silicone oil-in-water microemulsions prepared via the following steps:
1. A primary surfactant is dissolved in water.
2. A siloxane is added, and a two-phase mixture is formed.
3. With simple mixing, a co-surfactant is slowly added to the two-phase mixture, until a clear isotropic microemulsion of a siloxane-in-water is formed. These systems typically can have a mean particle size of less than about 20 nanometer, and a narrow particle size distribution.

Thus, siloxanes can, for example, be added to solutions containing ionic surfactants, such as dodecyltrimethyl ammonium bromide (DTAB) and sodium dodecyl sulfate (SDS), until a two-phase system is formed. A co-surfactant, such as 1-pentanol, is then titrated into the solution, until a clear, isotropic microemulsion results. Salts such as sodium chloride can also be included.

The system can be polymerized by the addition of, for example, a strong acid or a strong base ring-opening polymerization catalyst or a condensation polymerization catalyst. The use of such a thermodynamically stable preemulsion leads to a vastly simplified polymerization process. Some benefits, for example, include fast polymerization rates and high molecular weights. In some instances, a very low molecular weight polydispersity has been observed.

In particular, this embodiment provides a method of making a thermodynamically stable, clear, silicone oil-in-water microemulsion, by (i) forming a two-phase mixture obtained by combining water, a siloxane, and a nonionic surfactant, a cationic surfactant, or an anionic surfactant; (ii) adding to the two-phase mixture a co-surfactant selected from the group consisting of monohydroxy alcohols, diols, and triols, until a thermodynamically stable, clear, pre-microemulsion containing the siloxane is formed; (iii) adding a polymerization initiator to the thermodynamically stable, clear, pre-microemulsion; (iv) heating the thermodynamically stable, clear, pre-microemulsion; (v) agitating the heated, thermodynamically stable, clear, pre-microemulsion; and (vi) allowing the siloxane to polymerize, until a thermodynamically stable, clear, microemulsion is formed containing a higher molecular weight silicone polymer.

The organosilicon precursors which are used in the process according to this embodiment of the invention include as the essential ingredient, (i) the organofunctional cocyclic siloxane, i.e., the dialkyl, alkyl carboxyalkyl cocyclic siloxane. Optionally, the reaction mixture may also contain organosilicon precursors discussed above such as (ii) the C$_8$ or more carbon atom containing alkylmethyl, dimethyl silicone cocyclic, (iii) the short chain linear silicone endblocker, and (iv) the dialkyl cyclosiloxane.

Silicone copolymers according to this embodiment can be prepared using only the organosilicon precursor (i), while the silicone terpolymers require the presence of at least organosilicon precursors (i) and (ii). Silicone copolymers can also be prepared using organosilicon precursors (i) and (iv), if desired. When the short chain linear silicone endblocker (iii) is included in the reaction mixture, its presence results in the formation of trialkylsiloxy endblocked silicone copolymers and silicone terpolymers, rather than silanol endblocked silicone copolymers and silicone terpolymers, as would be the case in its absence.

A surfactant(s), a cosurfactant(s), and a polymerization initiator, are required for the reaction to proceed and for forming a microemulsion, and reference may be had to the copending application for a detailed list of each of these components.

Generally, preferred nonionic surfactants are alcohol ethoxylates of the formula R8-(OCH$_2$CH$_2$)$_t$OH in which R8 is a fatty hydrocarbon residue of 8–20 carbon atoms, and t has a value of 1–100. Representative anionic surfactants are sulfonic acids; salt derivatives of sulfonic acids; alkali metal sulfosuccinates; sulfonated glyceryl esters of fatty acids; salts of sulfonated monovalent alcohol esters; amides of amino sulfonic acids; sulfonated products of fatty acid nitriles; sulfonated aromatic hydrocarbons; condensation products of naphthalene sulfonic acids and formaldehyde; sodium octahydro anthracene sulfonates; alkali metal alkyl sulfates; ether sulfates having alkyl groups of at least eight carbon atoms; and alkylaryl sulfonates having one or more alkyl groups of at least eight carbon atoms. Some suitable cationic surfactants include compounds containing quaternary ammonium hydrophilic moieties in the molecule which are positively charged, such as quaternary ammonium salts represented by R9R10R11R12N$^+$X$^-$ where R9 to R12 are alkyl groups containing 1–30 carbon atoms, or alkyl groups derived from tallow, coconut oil, or soy; and X is halogen, i.e., chlorine or bromine.

The co-surfactant is generally a compound such as a monohydroxy alcohol, a diol, or a triol. Some preferred co-surfactants include 1-butanol, 1-pentanol, 1-decanol, 1-hexadecanol, ethylene glycol, propylene glycol, trimethylene glycol, and glycerol. The catalyst is a material capable of polymerizing siloxanes in the presence of water, including materials generally known as condensation polymerization catalysts capable of cleaving siloxane bonds. Representative condensation polymerization catalysts include strong acids such as substituted benzene sulfonic acids, aliphatic sulfonic acids, hydrochloric acid, and sulfuric acid; and strong bases such as quaternary ammonium hydroxides, and metal hydroxides such as sodium hydroxide.

EXAMPLE

Microemulsion Polymerization

The following example illustrates the third embodiment of this invention in more detail. In this example, a cationic surfactant was used comprising dodecyltrimethyl ammonium bromide (DTAB) $CH_3(CH_2)_{11}N^+(CH_3)_3Br^-$. The co-surfactant was primary amyl alcohol, i.e., 1-pentanol $CH_3(CH_2)_4OH$. The polymerization initiator, i.e., the catalyst, was hydrochloric acid.

Example 5

Preparation of a Microemulsion 0.73 gram of the organofunctional cocyclic siloxane and 3.34 gram of a solution containing about 22 percent by weight of DTAB cationic surfactant were added to a glass vial equipped with a stirring bar, and 0.92 gram of co-surfactant 1-pentanol were titrated into the vial dropwise, with mixing, until a thermodynamically stable, clear, pre-microemulsion, had formed. Polymerization of the organofunctional cocyclic siloxane was catalyzed by adding 0.02 gram of a 35 percent by weight aqueous HCl catalyst solution. The temperature was adjusted to about 70° C. The reaction was allowed to proceed to completion, whereupon the contents of the vial were neutralized with triethanolamine. The OH endblocked silicone copolymer was recovered from the microemulsion by breaking the product using a salt. The silicone copolymer was isolated and analyzed by Gel Permeation Chromatography (GPC).

The conditions used in preparing the microemulsion, and the characteristics of the silicone copolymer are summarized in Table 1. In Table 1, alpha ($\alpha$) is the weight percent of the siloxane oil÷the weight percent of the siloxane oil+the weight percent of water. Gamma ($\gamma$) is the weight percent of the cationic surfactant S1+the weight percent of the co-surfactant S2÷the weight percent of the siloxane oil+the weight percent of water +the weight percent of the cationic surfactant S1+the weight percent of the co-surfactant S2. The data in Table 1 is based upon preparation of a composition having a total mass of ten gram.

The silicone copolymer was characterized and is shown in Table 1 by its polydispersity, i.e., $DP_w/DP_n$. Polydispersity can be expressed in terms of $DP_n$ and $DP_w$ rather than the number-average molecular weight $M_n$ and weight-average molecular weight $M_w$, and this terminology has been used in Table 1. DP, it is noted, is the degree of polymerization in the silicone copolymer, indicating the number of repeating units present in the polymer species. The silicone copolymer in the composition according to this embodiment of the invention most preferably have average droplet diameters of less than about 50 nanometer (0.050 micron $\mu$m) to provide optical clarity. The criteria used to determine clarity, and the term Clear in Table 1, is whether text can be read with the naked eye through a two centimeter diameter bottle filled with the microemulsion.

TABLE 1

| EXAMPLE | S1 | S2 | $\alpha$ | $\gamma$ | Particle Size, $\mu$m | Appearance |
|---|---|---|---|---|---|---|
| 5 | DTAB | $C_5H_{11}OH$ | 0.2 | 0.33 | 0.0126 | Clear |

| EXAMPLE | Catalyst | Reaction Temp. ° C. | $DP_n$ | $DP_w$ | Polydispersity |
|---|---|---|---|---|---|
| 5 | HCl | 70 | 6.7 | 7.2 | 1.029 |

The compositions, emulsions, and microemulsions, according to this invention have application in the personal care arena, especially in the care of hair, where conditioning is desirable. Thus, they can be used in hair shampoos, hair conditioners, hair sprays, mousses, permanents, depilatories, and cuticle coats, to enhance gloss and provide conditioning benefits.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:
1. A method of preparing a silicone copolymer or a silicone terpolymer comprising heating a mixture of (i) an organofunctional cocyclic siloxane having the formula

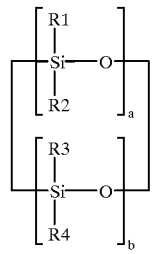

where R1 to R3 are each an alkyl group containing 1–6 carbon atoms; R4 is a carboxyalkyl or carboxyalkyl derivative group having the formula —$(CHR5)_n COOR6$ where R5 is hydrogen or an alkyl group containing 1–6 carbon atoms; R6 is hydrogen, an alkyl group containing 1–6 carbon atoms, or a trialkylsilyl group —$Si(R7)_3$ in which R7 is an alkyl group containing 1–6 carbon atoms; a and b are each a positive integer having a value of 1–10; and n is a positive integer having a value of 3–20; and optionally (ii) an alkylmethyl, dimethyl silicone cocyclic wherein the alkyl contains eight or more carbon atoms, in the presence of (iii) an acid catalyst, at a temperature and for a time sufficient to cause polymerization of (i) and optionally (ii) to the desired silicone copolymer and silicone terpolymer, respectively.

2. A method according to claim 1 in which the mixture further includes (iv) a short chain linear silicone endblocker; (v) a dialkyl cyclosiloxane; or mixtures therof.

3. A method according to claim 1 in which the acid catalyst is a mineral acid, an acid clay, a Lewis acid, an alkane sulfonic acid, or a perfluoroalkane sulfonic acid.

4. A method according to claim 1 in which the alkylmethyl, dimethyl silicone cocyclic has a structure corresponding to the formula:

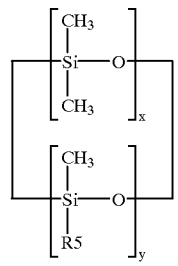

where x and y are integers having a value of 1 to about 10; and R5 is a hydrocarbon group containing eight or more carbon atoms.

* * * * *